United States Patent [19]
McClure et al.

[11] Patent Number: 5,931,807
[45] Date of Patent: Aug. 3, 1999

[54] MICROWAVE-ASSISTED LIPOSUCTION APPARATUS

[75] Inventors: Richard J. McClure, San Diego, Calif.; John M. Osepchuk, Concord, Mass.; Tulio Parisi, San Diego; R. Kemp Massengill, Poway, both of Calif.

[73] Assignee: Sonique Surgical Systems, Inc., Escondido, Calif.

[21] Appl. No.: 08/843,664

[22] Filed: Apr. 10, 1997

[51] Int. Cl.$^6$ ..................................................... A61M 1/00
[52] U.S. Cl. ................................................................ 604/27
[58] Field of Search .............................. 604/280, 22, 27, 604/30, 31, 35, 43, 49, 50–53, 118, 114, 246, 247

[56] References Cited

U.S. PATENT DOCUMENTS

| | | | |
|---|---|---|---|
| 4,583,556 | 4/1986 | Hines et al. | 128/804 |
| 4,825,880 | 5/1989 | Stauffer et al. | 128/804 |
| 5,295,955 | 3/1994 | Rosen et al. | |
| 5,447,510 | 9/1995 | Jensen . | |
| 5,501,655 | 3/1996 | Rolt et al. | |
| 5,503,150 | 4/1996 | Evans . | |
| 5,507,790 | 4/1996 | Weiss | 607/100 |
| 5,522,869 | 6/1996 | Burdette et al. | 607/97 |
| 5,524,620 | 6/1996 | Rosenschein | 128/653.1 |
| 5,540,655 | 7/1996 | Edwards et al. | 604/22 |
| 5,540,683 | 7/1996 | Ichikawa et al. | 606/40 |
| 5,542,815 | 8/1996 | Edwards et al. | 604/22 |
| 5,542,916 | 8/1996 | Hirsch et al. | 604/22 |
| 5,549,639 | 8/1996 | Ross | 607/101 |
| 5,555,887 | 9/1996 | Fraser et al. | 128/663.01 |
| 5,556,377 | 9/1996 | Rosen et al. | 604/22 |
| 5,573,497 | 11/1996 | Chapelon | 601/2 |
| 5,599,295 | 2/1997 | Rosen et al. | 604/22 |
| 5,660,836 | 8/1997 | Knowlton | 424/400 |
| 5,683,382 | 11/1997 | Leniban et al. | 606/33 |

FOREIGN PATENT DOCUMENTS

| | | |
|---|---|---|
| 96/34569 | 11/1996 | WIPO . |
| 96/36288 | 11/1996 | WIPO . |
| 96/36397 | 11/1996 | WIPO . |

OTHER PUBLICATIONS

Dickinson, R.J., *Measurement of Changes in Tissue Temperature Using MR Imaging*, pp. 468–472, May 1986, Journal of Computer Assisted Tomography.

Goldblith, S.A., *Microwaves, an Annotated Bibliography*, pp. 43–75, date and place of publication unknown.

Harvey, A.F., *Industrial, Biological and Medical Aspects of Microwave Radiation*, pp. 557–566, Oct. 1959, place of publication unknown.

Labonte, S., *Monopole Antennas for Microwave Catheter Ablation*, pp. 1832–1840, Oct. 1996, IEEE Transactions on Microwave Theory and Techniques.

Osepchuk, J., *Microwave Technology*, pp.672–675 and 677–699, 1995, Encyclopedia of Chemical Technology, Fourth Edition.

Schwan, H.P., *Variations between Measured and Biologically Effective Microwave Diathermy Dosage*, pp. 363–370, Sep. 1954, Archives of Physical Medicine and Rehabilitation.

*Primary Examiner*—Manuel Mendez
*Attorney, Agent, or Firm*—Gerald W. Spinks

[57] ABSTRACT

A method and apparatus for heating fatty tissue to facilitate liposuction removal of fat and, by additional heating, to enable denaturing of the tissue structure. The apparatus uses microwave energy, applied by a cannula to the fatty tissue, as a means to facilitate fat removal. The microwave energy is delivered at a frequency range chosen to optimize energy coupling directly to the fatty tissue, while insuring the attenuation of the radiation level to a safe level in a relatively short distance. The cannula is provided with internal channels to simultaneously provide fluid and remove the mixture of fluid and fatty tissue. Since the microwave frequency is selected to insure direct coupling with the fat tissue, it is not necessary to introduce water to promote coupling, and if water is introduced for cooling or irrigation purposes, no salts need to be added to the water for purposes of microwave energy coupling.

11 Claims, 3 Drawing Sheets

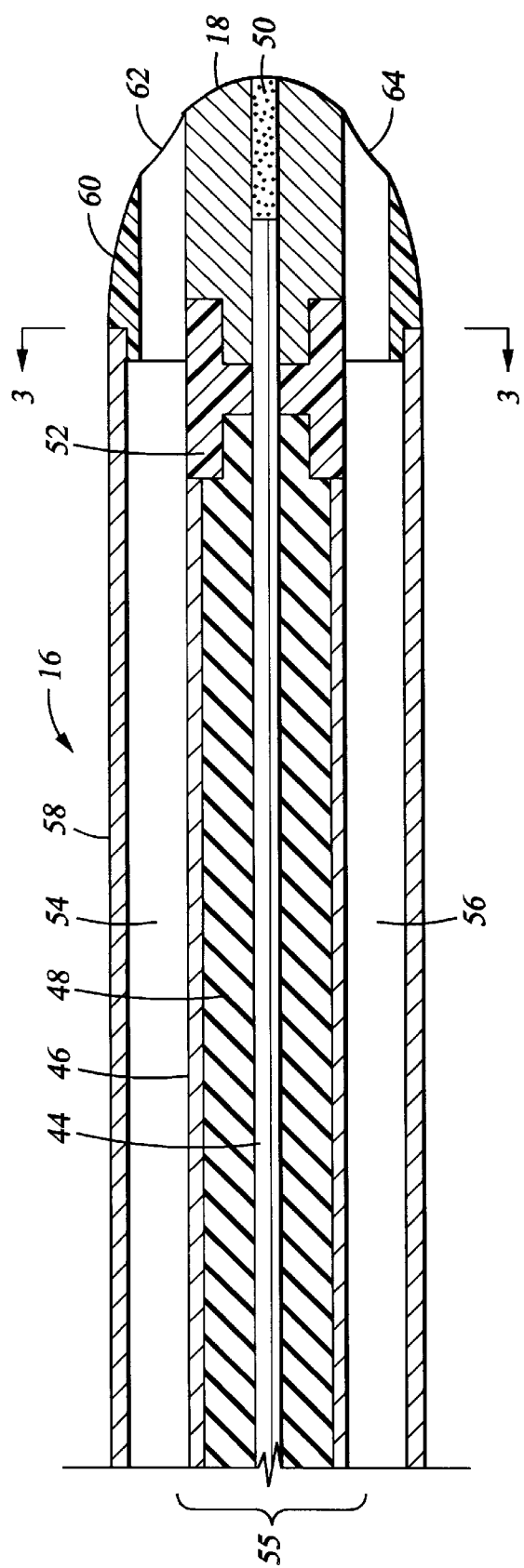
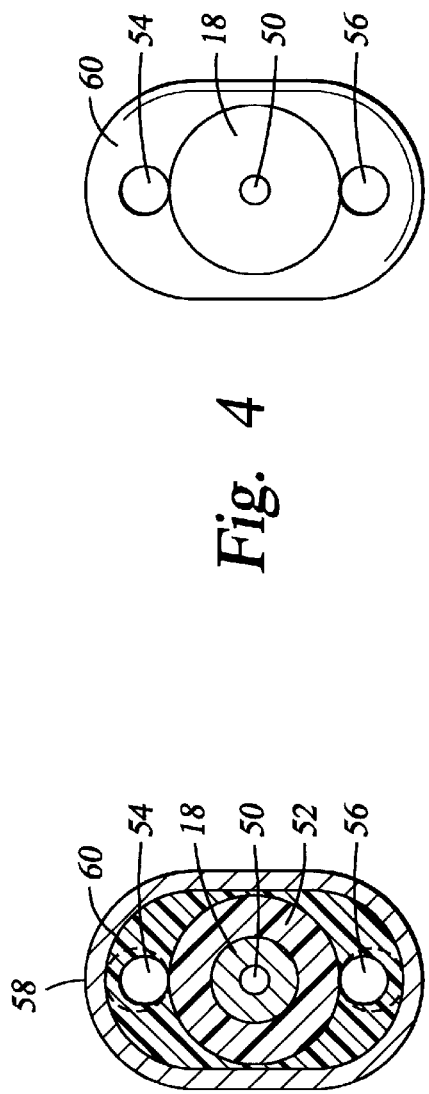
Fig. 2
Fig. 4
Fig. 3

MICROWAVE-ASSISTED LIPOSUCTION APPARATUS

CROSS REFERENCE TO RELATED APPLICATIONS

Not Applicable

FEDERALLY SPONSORED RESEARCH OR DEVELOPMENT

Not Applicable

BACKGROUND OF THE INVENTION

This invention is directed to an apparatus and method for heating fat tissues for medical purposes, such as body contouring and weight reduction by removal of unwanted fatty deposits.

Obesity is one of the most common conditions experienced by men and women in the United States and it is rapidly becoming a worldwide phenomenon. Obesity is generally defined as being overweight by 30% or more; 100% overweight is quite common; and 200% overweight is not rare. One case of 500% overweight has been treated surgically, with removal of 150 kilograms of fat in one procedure. Since the advent of liposuction, there has been a steady world wide growth of cosmetic surgery, now accelerated by the addition of the ultrasonic procedure, to several hundred thousand surgeries per year.

Obesity is a condition which arises from the natural bodily function of storing energy from food ingested during excess availability, to provide for times of shortage. To some extent, the body will attempt to store fat without limit. Huge amounts of money are expended to remove fat by diet, exercise, and surgery. Dieting is generally unsatisfactory, because it is very reversible; exercise is slow and repugnant to many. Surgery is a faster solution, but traumatic, and, if used to excess, can be life threatening.

Initially, the popular practice in liposuction surgery was to use a vacuum aspiration source connected to a tube, or cannula, fitted with a handle, and to plunge the cannula, in a tunneling mode, vigorously into the body where fat deposits were to be removed. The physical damage to the fatty tissue liberated fat and blood in approximately equal quantities. Most recipients of this treatment did so for cosmetic improvement, or contouring. An improvement of the procedure was disclosed in U.S. Pat. No. 4,886,491, in which ultrasonic energy was supplied to the cannula, making the liberation of fat significantly less traumatic, because of a reduction in the loss of blood, better fat cell melting/liquefaction, and less tissue damage. This has enabled greater quantities of fat to be aspirated, with a limited amount of trauma, and it has reduced the physical effort required of the surgeon, since the cannula tends to part the tissue as it penetrates. In both the original and the ultrasonic-aided liposuction procedures, fat cells are removed so that they are no longer available as locations for the storage of fat. Unless the body generates more fat cells, the reduction of fat storage capability is permanent.

Fatty tissue is made up of an ensemble of small vesicles, or adipocytes, each having a wall of protein forming a "skin". Adjacent adipocytes appear to share these walls in such a way as to form a larger structure, similar to a foam. These can vary from $\frac{1}{10}$ mm to several millimeters in diameter. If the wall protein is removed, the reduction of fat storage capacity is permanent. If the wall protein is heated enough to "denature" the protein, such as in excess of 43° C., the reduction is also permanent. If the wall is merely damaged, the potential exists for regeneration of the fat storage ability.

Recently, microwave treatment of tissue to curtail growth has been successfully demonstrated, for example, in cancerous tumors, benign tumors, and enlarged prostate glands, without damage to adjacent organs and without removal of the treated tissue. The denaturing of tissue in these examples is confined to the tissues targeted.

BRIEF SUMMARY OF THE INVENTION

The device and method of this invention provide a controlled medical treatment which is suitable for heating tissue to facilitate liposuction removal of fat and, by further heating, to enable denaturing of the tissue structure so that additional fat will not be stored therein. The apparatus and method can be used to destroy and remove fat tissue in any location which is accessible to a percutaneous catheter.

The presently disclosed apparatus uses microwave energy, applied by a cannula to the fatty tissue, as a means to facilitate fat removal. The microwave energy is delivered at a frequency range chosen to optimize energy coupling to the fatty tissue, while insuring the attenuation of the radiation to a safe level within a relatively short distance. The microwave energy is delivered at a power level appropriate for heating a sufficient volume of the tissue for practical fat removal rates.

The cannula is provided with internal channels, which can simultaneously provide fluid infusion and also the removal of the mixture of fluid and fatty tissue. Water is one fluid which can be used, to aid in the fat removal and to assist in temperature control of both the tissue being heated and the cannula itself. Since the microwave frequency is selected to insure direct coupling with the fat tissue, it is not necessary to introduce water to promote coupling, and if water is introduced for cooling or irrigation purposes, no salts need to be added to the water for purposes of microwave energy coupling. However, it may be convenient to add anesthetic or electrolytes, for patient care. To avoid the trauma of cutting tissue during cannula entry and forward strokes, the end of the cannula is made bullet shaped. This causes the cannula to gently part, rather than to tear, tissue.

A primary object of the invention is to provide an apparatus and method for safer and faster removal of fat than is done with conventional liposuction methods. The microwave antenna of the present invention heats tissue radially, and its energy is absorbed over a volume approximately 10 times as great as in currently known devices, so the energy concentration is less intense and less likely to cause local burning of tissue.

It is also an object of the invention to provide a device for limiting the heating action to the target site, thereby minimizing the trauma to intervening tissues, and achieving a greater medical benefit.

It is another object of the invention to provide a medical probe device with a microwave monopole antenna at the distal end thereof for local denaturing of fatty tissue structure.

It is still another object of the invention to provide a medical probe device which can deliver cooling and irrigation fluid, anesthetic, antiseptic, or electrolyte to the site of the fatty tissue removal.

In summary, the device of this invention is a medical probe apparatus comprising a cannula having a distal tip equipped with a monopole antenna, fed via a coaxial cable with microwave power to enable heating and denaturing of fatty tissue for removal by aspiration. The cannula and cable are also cooled by fluid passing through the cannula to irrigate the fatty tissue. The coaxial cable and the inflow and outflow channels are arranged in a parallel, contiguous fashion inside the cannula, and these elements are connected externally to microwave, fluid, and vacuum sources, respectively. In a preferred embodiment, the cannula is oval or elliptical in shape, so as to accommodate the cable, inflow, and outflow channels side by side, in a configuration suitable for the least traumatic entry wound. The level of microwave power to the antenna is controlled by the surgeon by altering the duty cycle, and the power is preferably supplied at a frequency of approximately 2.45 gigahertz±10%.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 2 is a partial longitudinal sectional view of the distal end of the cannula of the probe shown in FIG. 1;

FIG. 3 is a transverse sectional view of the distal end of the cannula shown in FIG. 2;

FIG. 4 is an end view of the cannula shown in FIG. 2;

DETAILED DESCRIPTION OF THE INVENTION

The device of this invention provides a variable and controllable amount of localized heating of fatty tissue in order to facilitate its removal from obese patients. The antenna illustrated herein as part of the preferred embodiment is a monopole antenna, but the term antenna as used hereinafter is intended to include both monopole and dipole structures for the local application of microwave power to the fat tissue. The antenna and its housing, a flattened bullet shaped plastic assembly, comprise the distal tip of the hand-held cannula. The power to the antenna is conducted via external coaxial cable from the power supply, to a disconnectable interface at the proximal end of the handpiece, where it connects to the cannula coaxial conductor, and thence to the antenna.

Figure 1:
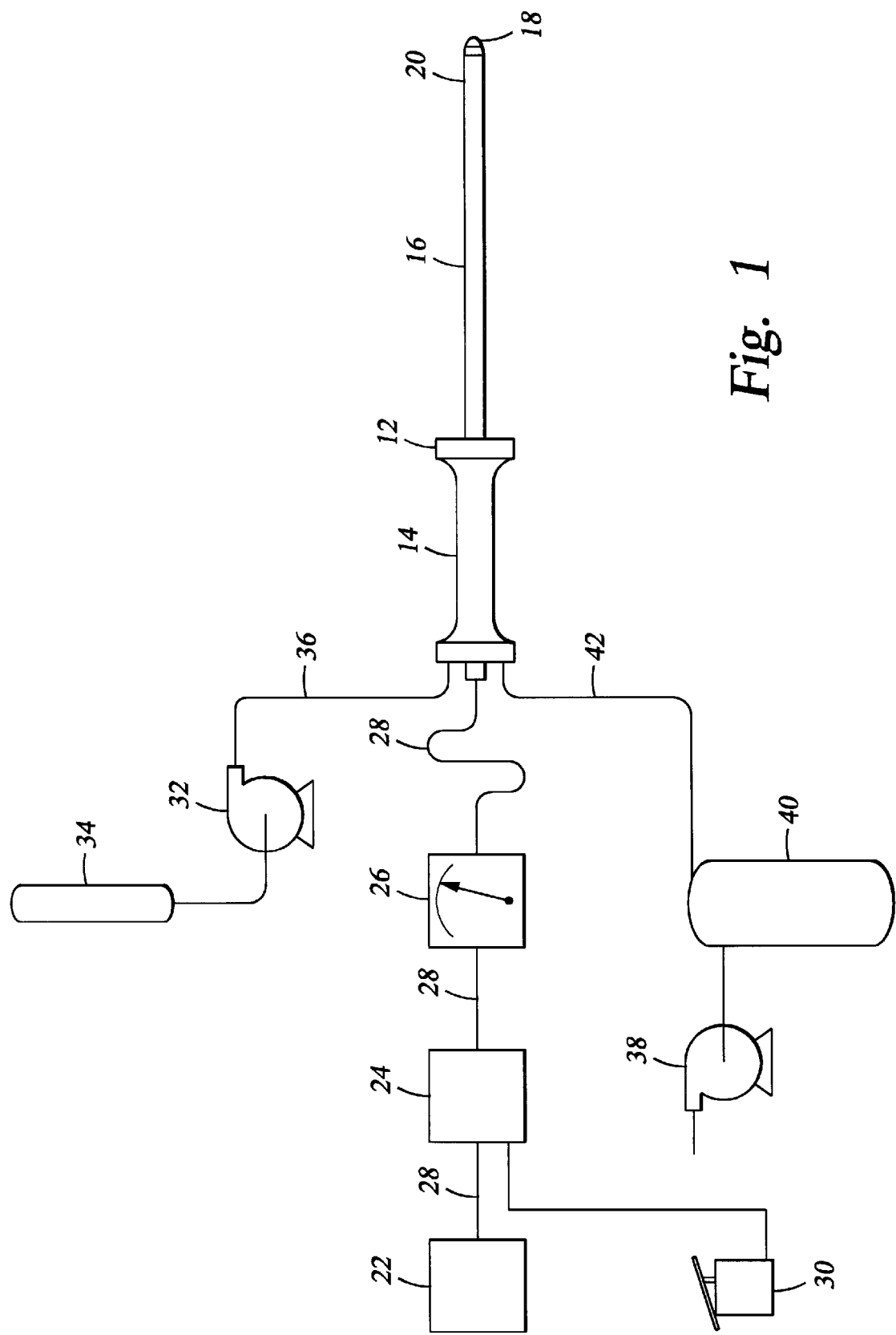
FIG. 1 is a schematic of the microwave-assisted liposuction system according to the present invention.

FIG. 1 is a schematic of a system 10 for implementation of this invention, consisting essentially of a probe 12, a microwave generator 22, a fluid source 32, and a vacuum source 38. The microwave generator 22 sends microwave energy through a duty cycle controller 24 and a power meter 26 to the probe 12. The generator 22 operates at a constant power level. The duty cycle controller 24 is operated by a foot control 30 to allow the surgeon to turn the microwave generator 22 on and off, thereby regulating the amount of microwave energy supplied to the probe 12. The microwave energy is fed via a flexible coaxial cable 28 from the generator 22 to a disconnect on the proximal end of a handpiece 14 of the probe 12. The microwave energy is thence supplied to a cannula 16 on the probe 12, and to an antenna applicator 18 on the distal end of the cannula 16, via another coaxial conductor within the cannula 16. A fluid supply 32, shown as a pump, is connected by a supply hose 36 to a fluid reservoir 34, and to the handpiece 14. As will be discussed below, a fluid flow path is provided through the probe 12 to a fluid outflow port near the distal end of the probe 12, near the antenna 18. The fluid can be supplied for a variety of purposes, including intumescence of the fat tissue, cooling of the coaxial conductor in the probe 12, delivery of anesthetic to the fat removal area, and delivery of electrolyte for patient treatment. Because of the frequency selected for the output of the microwave generator 22, it is not necessary to provide fluid to the vicinity of the antenna 18 for coupling purposes. A vacuum source 38, shown as a vacuum pump, is connected by a suction hose 42, through a fluid collector 40, to the handpiece 14. As will be discussed below, a vacuum flow path is provided from a vacuum inflow port near the distal end of the probe 12, near the antenna 18, through the probe 12 to the connection point of the suction hose 42. The vacuum can be applied to remove liquefied fat tissue and other fluids from the area near the antenna 18.

The cannula 16 is inserted through intervening tissue to place the antenna 18 at the desired location in the subcutaneous fatty layer, in order to deliver microwave energy to facilitate removal of the fat. In particular, this apparatus is most applicable to extensive thicknesses of fat, such as are found in obese people, where its capability for high power level heating is best utilized for rapid removal of large volumes of fat.

The microwave generator 22 provides the microwave energy via the coaxial conductors to the antenna 18. The amount of microwave energy applied to the antenna 18, in a preferred embodiment of the apparatus, is controlled by varying the duty cycle of the generator 22. Essentially, the surgeon controls the average power via the on/off ratio, or duty cycle, by turning the generator 22 on and off, by manipulating the foot control 30. The frequency of the microwave energy itself is provided at an essentially constant level of 2.45 gigahertz±10%.

The frequency of 2.45 gigahertz is selected because (a) it is especially efficient for heating biological tissue, and (b) the energy absorption rate for this frequency, in fatty tissue, is such that the power density may be high near the antenna 18, for fast heating of the fat, and yet the power density will fall off rapidly enough to a safe level, so as to avoid damage to adjacent muscle tissue, or other organs in the vicinity. For plane wave propagation, fatty tissue absorption of 2.45 gigahertz energy reduces the power density of the propagated wave to approximately one third of its initial value, at a distance of about one inch from the antenna 18. Additional loss is achieved by virtue of the cylindrical shape of the antenna 18, which radiates radially, so that power density also experiences a geometric loss proportional to the distance from the antenna 18. The antenna 18 provides a cylindrical zone of heating, with the axis of the heated zone being parallel to the axis of the cannula 16. The power density in the heated zone falls off geometrically as 1/r, coupled with an exponential decrease due to absorption, limiting significant heating to about a one inch distance in fatty tissue.

If a power density of 2000 watts/square inch is established at the antenna surface, it will reduce to 50 watts/square inch at a distance of one inch from the antenna 18. This is a reduction in power density by a factor of 40. The selected value of 2000 watts/square inch for a representative size of antenna 18 assumes that the antenna conductor element is in intimate contact, at all points of its exposed surface, with the fatty tissue. Intimate contact is necessary to ensure a good impedance match with the generator 22. Since the generator 22 delivers its power to the antenna 18 via coaxial conductors, in the event of an imperfect impedance match, much of the power will be reflected back to the generator 22, and some of that will cause heating of the coaxial conductors. This can occur, for instance, if the antenna 18 is not completely immersed in tissue. In this condition, the fluid flow to the end of the cannula 16, and flow of fluid and fatty tissue back through the cannula 16, prevent overheating of the coaxial conductor and the cannula 16.

FIG. 2 is a partial longitudinal sectional view of the distal end of a preferred embodiment of the cannula 16. A hollow oval tubular jacket 58 houses a fluid supply channel 54, an aspiration return channel 56, and a coaxial conductor 55 therebetween. The jacket 58 is preferably constructed of stainless steel. The jacket 58 is terminated at its distal end by a flattened, bullet shaped, dielectric nosepiece 60, within which is secured the monopole antenna applicator 18. The dielectric nosepiece 60 can be constructed of a material such as polytetrafluorethylene. The coaxial conductor 55 comprises an inner axial conductor 44 surrounded by an outer shield 46, separated by a dielectric insulator 48. At the distal end of the coaxial conductor 55, the coaxial dielectric insulator 48 extends distally into a first recess in the proximal end of a cylindrical dielectric shroud 52. The shroud 52 can also be constructed of a material such as polytetrafluorethylene. A second recess in the distal end of the dielectric shroud 52 enshrouds the proximal end of the monopole antenna applicator 18. The antenna applicator 18 can be constructed of a conductive material such as tinned copper. The distal end of the axial conductor 44 is connected to the antenna applicator 18 by extending into an axial bore within the antenna applicator 18, with solder 50 being used to achieve a good conductive connection and fill the remainder of the axial bore.

To minimize the size of the entry wound, it is desirable to keep the cannula 16 small. A thickness of 5 to 6 mm. has been found acceptable, while 25 mm. would not be. The cannula 16 of the present invention is made oval, or elliptical, in shape, so as to accommodate the coaxial conductor 55 and provide supply and return channels 54, 56 for the fluids. A preferred embodiment has an elliptical cannula cross section with major and minor axes of approximately 10 mm. and 5 mm., respectively.

The cannula 16 is oval or elliptical in shape, and of such internal size that the coaxial conductor 55 forms a well-fitting divider between the two parallel channels 54, 56 through the cannula 16. These channels 54, 56 are provided to conduct fluid, via a distal supply port 62, into the vicinity where the fatty tissue is to be removed, and to aspirate fluid, via a distal aspiration port 64, out of the vicinity where fatty tissue is to be removed. The coaxial conductor 55 acts as a septum separating the channels 54, 56 from each other. The coaxial conductor 55 can be fixed to the cannula jacket 58 by fillets of epoxy on each side. If desired, tubular members could be positioned alongside the conductor 55 during fabrication to form the channels 54, 56, and then removed after fabrication, leaving open channels 54, 56. The fluid channels 54, 56 are in good thermal contact with the exterior of the coaxial conductor 55. Heat generated in the coaxial conductor 55 can be removed by the fluid flow, in both channels 54, 56. The temperature of the inlet fluid can be controlled to suit the application needs.

FIG. 3 is a transverse sectional view of the distal end of the cannula 16. The stainless steel cannula jacket 58 surrounds the proximal skirt of the nosepiece 60. The nosepiece 60 surrounds the fluid supply channel 54 and the vacuum return channel 56, with the shroud 52 and the proximal end of the antenna applicator 18 therebetween.

FIG. 4 a is an end view of the nosepiece 60, showing the distal end of the fluid supply channel 54, and the distal end of the vacuum return channel 56. Also shown are the distal end of the antenna applicator 18 and its axial bore, filled with solder 50.

Figure 5:
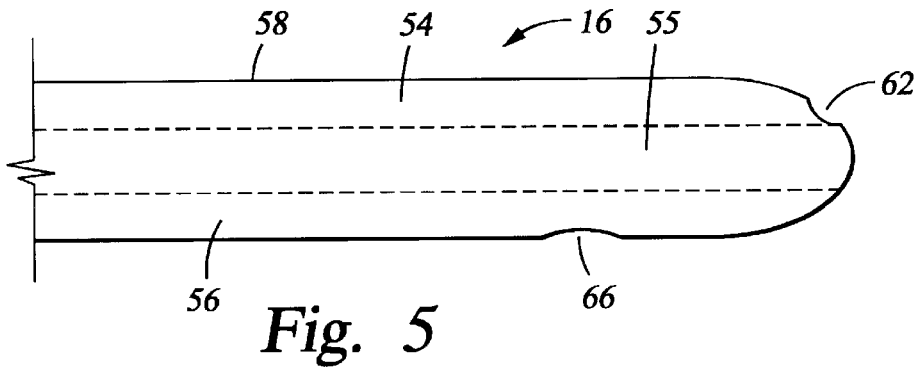
FIG. 5 is a schematic of a second embodiment of the distal end of the cannula of the present invention.

FIG. 5 shows a second embodiment of the distal end of the cannula 16, which has no distal aspiration port 64 in the distal end of the cannula 16, but which has a side aspiration port 66 on the side of the cannula 16, leading into the vacuum channel 56.

Figure 6:
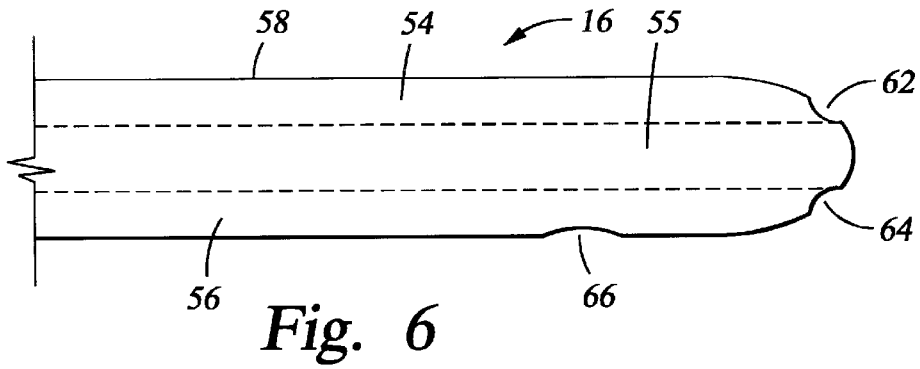
FIG. 6 is a schematic of a third embodiment of the distal end of the cannula of the present invention.

FIG. 6 shows a third embodiment of the distal end of the cannula 16, which has both a distal aspiration port 6 in the distal end of the cannula 16, and a side aspiration port 66 on the side of the cannula 16, leading into the vacuum channel 56.

Figure 7:
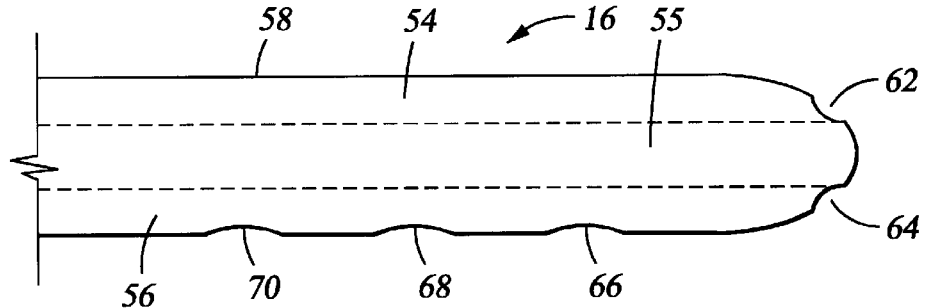
FIG. 7 is a schematic of a fourth embodiment of the distal end of the cannula of the present invention.

FIG. 7 shows a fourth embodiment of the distal end of the cannula 16, which in addition to the distal aspiration port 64 in the distal end of the cannula 16, also has a plurality of side aspiration ports 66, 68, 70 on the side of the cannula 16, leading into the vacuum channel 56.

Figure 8:
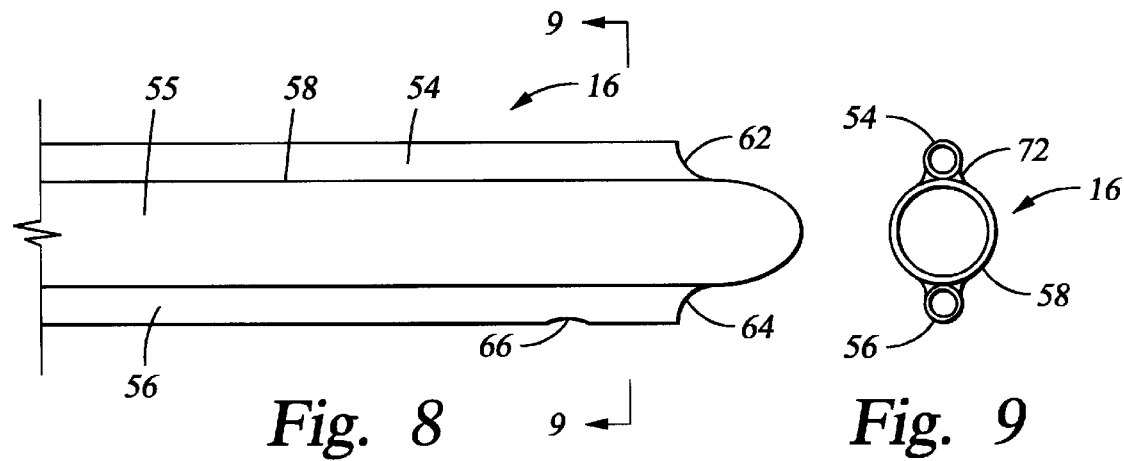
FIG. 8 is a schematic of a fifth embodiment of the distal end of the cannula of the present invention.

FIG. 8 shows a fifth embodiment of the distal end of the cannula 16, which has the fluid and vacuum channels 54, 56 attached to the external sides of the cannula jacket 58. Both a distal aspiration port 64 and a side aspiration port 66 are shown leading into the vacuum channel 56. As in the previous Figures, the aspiration ports can be located in various places.

Figure 9:
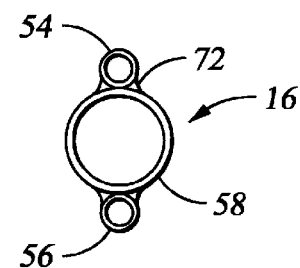
FIG. 9 is a transverse sectional view of the distal end of the cannula shown in FIG. 8.

FIG. 9 shows a sectional view of the distal end of the cannula 16 shown in FIG. 8, illustrating how the external channels 54, 56 can be attached to the cannula jacket 58 with fillets of epoxy or solder material 72.

During operation, microwave power is generated at a power level of approximately 500 watts by the generator 22 and conducted to the antenna 18. This results in a power density at the exposed surface of the antenna 18 of approximately 2000 watts/square inch. The surgeon controls the total energy applied, by manipulating the foot control 30 to turn the generator 22 on and off as the probe 12 is manipulated to position the antenna 18 in the desired locations. The microwave energy radiates into the surrounding fatty tissue and heats and denatures the fat cells to assist in liquefying the fat. The microwave energy is coupled directly to the fatty tissue, without the need for added water, to generate heat in the cylindrical volume surrounding the antenna applicator 18. As the cannula 16 is advanced through the tissue, liquid fat is liberated. Fluid can be conducted from the reservoir 34, via the fluid supply channel 54, to the vicinity of the antenna 18, as needed for irrigation, cooling, anesthesia, or control of patient electrolytes. Liquefied fat and other fluids are aspirated from the vicinity of the antenna 18, via the aspiration channel 56, to the fluid collector 40. The surgeon operates the power duty cycle control to suitably regulate the temperature at the antenna surface. Fluid flow can be maintained until the end of the procedure, if needed for cooling of the coax 55 and the cannula 16.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for removal of fat tissue from a patient, comprising:

an elongate cannula;

a monopole antenna mounted to a distal end of said cannula;

a coaxial cable mounted within said cannula, said coaxial cable having an axial conductor connected to said monopole antenna;

an irrigation channel mounted along a first external side of said coaxial cable within said cannula, said irrigation channel having an outlet port adjacent said distal end of said cannula, said irrigation channel being arranged in thermal contact with said coaxial cable;

an aspiration channel mounted along a second external side of said coaxial cable within said cannula, said aspiration channel having an inlet port, said aspiration channel being arranged in thermal contact with said coaxial cable;

a microwave generator connected to said axial conductor, said generator being capable of producing microwave radiation with a power density of approximately 2000 watts/square inch, ±10%, at a frequency of approximately 2.45 gigahertz, ±10%.

2. An apparatus for removal of fat tissue from a patient, as recited in claim 1, wherein said aspiration channel inlet port is located in said distal end of said cannula.

3. An apparatus for removal of fat tissue from a patient, as recited in claim 1, wherein said aspiration channel inlet port is located along a side of said cannula.

4. An apparatus for removal of fat tissue from a patient, as recited in claim 1, further comprising a plurality of said aspiration channel inlet ports located along a side of said cannula.

5. An apparatus for removal of fat tissue from a patient, as recited in claim 1, further comprising:

at least one said aspiration channel inlet port located along a side of said cannula; and an aspiration channel inlet port located in said distal end of said cannula.

6. An apparatus for removal of fat tissue from a patient, as recited in claim 1, wherein:

said cannula has an elliptical cross section;

said coaxial cable is located along a central axis of said cannula;

said irrigation channel is located along a first side of said coaxial cable; and said aspiration channel is located along a diametrically opposite side of said coaxial cable from said irrigation channel.

7. An apparatus for removal of fat tissue from a patient, as recited in claim 1, further comprising a source of irrigation fluid connected to said irrigation channel.

8. An apparatus for removal of fat tissue from a patient, as recited in claim 1, further comprising a vacuum source connected to said aspiration channel.

9. An apparatus for removal of fat tissue from a patient, as recited in claim 1, further comprising a bullet-shaped tip formed around said antenna on said distal end of said cannula.

10. An apparatus for removal of fat tissue from a patient, comprising:

an elongate cannula, said cannula having an elliptical cross section;

a monopole antenna mounted to a distal end of said cannula;

a coaxial cable located along a central axis of said cannula, said coaxial cable having an axial conductor connected to said monopole antenna;

an irrigation channel located along a first external side of said coaxial cable within said cannula, said irrigation channel having an outlet port adjacent said distal end of said cannula;

an aspiration channel located along a diametrically opposite external side of said coaxial cable from said irrigation channel, within said cannula, said aspiration channel having an inlet port adjacent said distal end of said cannula;

a microwave generator connected to said axial conductor, said generator being capable of producing microwave radiation with a power density of approximately 2000 watts/square inch, ±10%, at the surface of said monopole antenna, at a frequency of approximately 2.45 gigahertz, ±10%, for coupling directly with said fat tissue without the addition of polar liquid, said power density of said microwave radiation being attenuated by said fat tissue by a factor of at least ten within approximately one inch of said monopole antenna.

11. A method of removing fat tissue from a patient, comprising:

providing a probe, a monopole antenna mounted to said probe and connected to a coaxial cable mounted within said probe, an irrigation channel mounted alongside said coaxial cable, and an aspiration channel mounted alongside said coaxial cable;

providing a microwave generator connected to said monopole antenna via said coaxial cable;

controlling said generator to produce microwave radiation at a frequency of approximately 2.45 gigahertz, ±10% and power level of approximately 2000 watts/square inch, ±10%;

supplying irrigation fluid to said area adjacent to said antenna via said irrigation channel; and aspirating liquefied fat tissue from said area adjacent to said antenna via said aspiration channel.

* * * * *